United States Patent [19]

Moore

[11] 4,418,074
[45] Nov. 29, 1983

[54] 2,6 DI(T-BUTYL)-4-(2'-PYRROL)-PHENOL AND ANTI-INFLAMMATORY USE THEREOF

[75] Inventor: George G. I. Moore, Houlton, Wis.

[73] Assignee: Riker Laboratories, Inc., St. Paul, Minn.

[21] Appl. No.: 324,061

[22] Filed: Nov. 23, 1981

[51] Int. Cl.³ .................. C07D 207/333; A61K 31/40
[52] U.S. Cl. ..................................... 424/274; 548/539
[58] Field of Search ................... 200/326.55; 548/539; 424/274

[56] References Cited

U.S. PATENT DOCUMENTS

| | | | |
|---|---|---|---|
| 2,171,159 | 8/1939 | McNally et al. | 260/326.5 J |
| 3,117,129 | 1/1964 | Boyle | 546/314 |
| 3,803,171 | 4/1974 | Carson | 260/326.5 J |
| 4,124,725 | 11/1978 | Moore | 424/330 |
| 4,128,664 | 12/1978 | Moore | 424/324 |
| 4,172,082 | 10/1979 | Moore | 549/72 |
| 4,172,151 | 10/1979 | Moore | 424/330 |
| 4,200,645 | 4/1980 | Goudie | 260/326.5 J |
| 4,222,883 | 9/1980 | Clinton | 252/52 R |

FOREIGN PATENT DOCUMENTS 1195628 7/1968 United Kingdom .

OTHER PUBLICATIONS

White and Glossman, *Prostaglandins*, 7, 123 (1974).
Adamkiewicz et al., *Canad. J. Biochem. Physiol.*, 33:332 (1955).
Selye, *Brit. Med. J.*, 2:1129 (1949).
Winter, *Proc. Exper. Biol. Med.*, 111:544 (1962).

*Primary Examiner*—Donald G. Daus
*Assistant Examiner*—D. B. Springer
*Attorney, Agent, or Firm*—Donald M. Sell; James A. Smith; Robert W. Sprague

[57] ABSTRACT

3,5-Di(t-butyl)-4-(2'-pyrrolyl)phenol has pharmacological activity as an antiinflammatory agent.

4 Claims, No Drawings

2,6 DI(T-BUTYL)-4-(2'-PYRROL)-PHENOL AND ANTI-INFLAMMATORY USE THEREOF

TECHNICAL FIELD

This invention relates to a substituted pyrrole compound, and to the use of such compound as an antiinflammatory agent.

BACKGROUND ART

I have previously synthesized and described several antiinflammatory compounds containing di(t-butyl)-phenol groups. Information regarding these compounds is contained in U.S. Pat. Nos. 4,128,664 (2,6-di(t-butyl)-phenol substituted in the 4-position by an N-substituted carboxamido group), 4,124,725 (2,6-di(t-butyl)phenol substituted in the 4-position by an optionally substituted benzoyl group), 4,172,151 (2,6-di(t-butyl)phenol substituted in the 4-position by an optionally substituted phenyl group), and 4,172,082 (2,6-di(t-butyl)phenol substituted in the 4-position with optionally substituted thiophenyl groups).

DISCLOSURE OF INVENTION

The above described compounds are antiinflammatory agents useful in the treatment of inflammation related conditions such as rheumatoid arthritis. Many of the above compounds also have activity as stabilizers against oxidation, and this characteristic may be related to the efficacy of the above compounds as antiinflammatory agents, although there is no present confirmation of this possibility. The 3,5-di(t-butyl)-4-hydroxyphenyl moiety found in each of the above compounds is also found in the well-known antioxidant 3,5-di(t-butyl)-4-hydroxytoluene (commonly referred to as butylated hydroxytoluene, or "BHT"), a substance which is frequently used as a food additive to extend the shelf life of processed foods. BHT itself has little or no pharmacological value as an antiinflammatory agent. Likewise, many other compounds containing groups derived from di(t-butyl)phenol have little or no pharmacological value, e.g., 2,6-di(t-butyl)phenol, 4-carboxamido-2,6-di(t-butyl)phenol, 4-(2-chlorobenzoyl)-2,6-di(t-butyl)phenol, 4-(5-carboxy-2-thenoyl)-2,6-di(t-butyl)phenol, 2,6-di(t-butyl)-4-phenylsulfonylphenol, 4-acetyl-2,6-di(t-butyl)phenol, and 4-n-octyl-2,6-di(t-butyl)phenol.

Compounds other than those already described in the above-mentioned patents containing 3,5-di(t-butyl)-4-hydroxyphenyl groups may also have pharmacological activity as antiinflammatory agents. However, at the present time there appear to be no rules by which one could correlate structural similarities between various compounds containing the 3,5-di(t-butyl)-4-hydroxyphenyl moiety with the presence of useful antiinflammatory activity in such compounds. New antiinflammatory compounds containing the 3,5-di(t-butyl)-4-hydroxyphenyl moiety must be discovered by trial and error synthesis and testing.

The present invention provides, in one aspect, a compound of the formula:

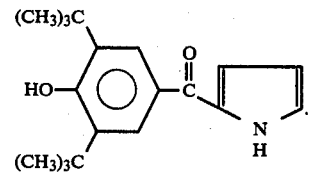

This compound has useful antiinflammatory activity. The present invention also provides antiinflammatory compositions containing such compound, and methods for combatting inflammatory reactions in mammals.

DETAILED DESCRIPTION

The compound of the invention can be prepared by reaction of 3,5-di(t-butyl)-4-hydroxybenzoyl chloride with salts of pyrrole. This reaction is generally carried out by dissolving the pyrrole compound in an inert solvent such as diethyl ether, carbon disulfide, tetrahydrofuran, dichloroethane, dichloromethane and the like, optionally under an inert gas atmosphere such as nitrogen, adding methylmagnesium bromide at a temperature below 0° C., adding the benzoyl chloride dropwise, and allowing the reaction to progress to completion. Heating or warming can sometimes be useful to promote the reaction. The preparation of the compound of the invention 2,6-di(t-butyl)-4-(2'-pyrroyl)phenol, is described in greater detail below in Example 1.

In addition to its use as effective antiinflammatory agents, the compound of the invention is relatively active as a stabilizer to prevent oxidation. It also has mild immunosuppressant activity.

In order to determine and assess pharmacological activity, testing in animals is carried out using various assays known to those skilled in the art. Thus, the antiinflammatory activity of the compound of the invention can be conveniently demonstrated using an assay designed to measure the ability of the compound to inhibit the enzyme prostaglandin synthetase (cyclooxygenase), such as the test described in White and Glossman, *Prostaglandins*, 7, 123 (1974). The antiinflammatory activity of the compound of the invention can also be demonstrated using an assay designed to test the ability of this compound to antagonize the local edema which is characteristic of the inflammatory response (the rat foot edema test). The compound of the invention is also active when administered dermally. Such topical activity has been measured by means of the guinea pig erythema test and by a contact sensitivity test. Antiinflammatory activity can also be detected by other assays known to the art such as the cotton pellet granuloma test and the adjuvant arthritis test.

Leading references to the rat foot edema method are:
(1) Adamkiewicz et al, *Canad. J. Biochem. Physiol.*, 33:332 (1955);
(2) Selye, *Brit. Med. J.*, 2:1129 (1949); and
(3) Winter, *Proc. Exper. Biol. Med.*, 111:544 (1962).

The edema test is performed on adult female rats. Generally, one group of 10 rats serves as non-medicated controls, while another group of 10 rats receives the test compound at various times prior to the induction of the edema, usually 15 minutes, one hour and/or 18 hours. The test compound is administered orally as a suspension in a 4 percent aqueous solution of acacia. Edema is induced by the plantar injection of 0.5 percent carrageenin (0.1 ml/foot) into the right hind foot. The left hind foot receives a like volume of 0.9 percent saline solution. Three hours later, the volume of each hind foot is determined plethysmographically. The edema is expressed as the increase in the volume of the edemogen injected foot less the volume of the saline injected foot. The percent inhibition is calculated by dividing the mean increase in the edema of the medicated group by the mean increase in the edema of the non-medicated group, subtracting this quotient from 1, and multiplying the resulting number by 100. An active dose is that giving a statistically significant inhibition of the induced edema, usually in the range of at least about 25–35 percent inhibition. The compound of the invention exhibits 71 percent inhibition in the above test at a dose of 100 mg/kg.

The compound of the invention preferably is administered orally but other known methods of administration can also be used, e.g., dermatomucosally (for example dermally, rectally and the like), parenterally (for example by subcutaneous injection, intramuscular injection, intraarticular injection, intravenous injection and the like), and by ocular administration. Effective dosages should be less than a toxic amount. Such dosages ordinarily fall within the range of about 1 to 500 mg of the compound of the invention per kg of body weight of the mammal to be treated. Oral dosages are usually below 100 mg/kg. The compound of the invention ordinarily is administered in the form of a composition containing the compound together with a pharmaceutically acceptable carrier. Suitable compositions for oral administration are in the form of liquids (such as 4 percent acacia and polyethylene glycol solutions), tablets (which can contain anhydrous lactose, microcrystalline cellulose, modified starch, calcium stearate and talc, as well as other conventional compounding agents together with the active antiinflammatory agents), solid suspensions and capsules. Pharmaceutically acceptable carriers for topical application include creams, gels, tapes and the like. Liquid formulations, such as solutions or suspensions of the active ingredient in inert carriers, can be used for dosage by injection.

Using the methods described above, the preparation of the compound of the invention is illustrated in the following example. The purpose of the example is to enable those skilled in the art to practice the invention, and it is not intended to limit in any way the scope of the invention.

EXAMPLE 1

To a stirred solution of 15.0 g (0.185 mole) of pyrrole in 500 ml of diethyl ether at $-30°$ C. under a nitrogen atmosphere was added 65 ml of 2.86 M methylmagnesium bromide (0.185 mole) in diethyl ether. After stirring for 45 minutes, 50 g (0.185 mole) of 3,5-di(t-butyl)-4-hydroxybenzoyl chloride was added in small portions to the reaction mixture while maintaining the temperature of the reaction mixture below $-30°$ C. After the chloride addition was completed, the mixture was stirred while allowing the temperature to rise to 25° C. After 16 hours, the reaction mixture was neutralized with ten percent hydrochloric acid solution, diluted with 500 ml of water and 500 ml of dichloromethane, and mixed thoroughly. The lower layer was decanted and the dichloromethane layer then heated and filtered while hot. The filtrate was dried and evaporated to provide a residue which was recrystallized twice from hexane, each recrystallization including treatment of the residue with decolorizing charcoal. The product was white 2,6-di(t-butyl)-4-(2'-pyrroyl)phenol, m.p. 156°–157.6° C.

| Analysis: | % C | % H | % N |
|---|---|---|---|
| Calculated for $C_{19}H_{25}NO_2$: | 76.2 | 8.4 | 4.7 |
| Found: | 76.8 | 8.5 | 4.6 |

Various modifications and alterations of this invention will be apparent to those skilled in the art without departing from the scope and spirit of this invention and the latter should not be restricted to that set forth herein for illustrative purposes.

What is claimed is:

1. The compound 2,6-di(t-butyl)-4-(2'pyrroyl)phenol.

2. An antiinflammatory composition, comprising an antiinflammatory effective amount of the compound according to claim 1, together with a pharmaceutically acceptable carrier.

3. A method for combatting inflammatory reactions in a mammal which comprises administering to said mammal an effective dose, less than a toxic amount, of a composition according to claim 2.

4. A method according to claim 3, wherein said composition is administered orally.

* * * * *